Dec. 15, 1953 M. L. V. VAN ZANTEN Plant Pat. 1,233
AZALEA PLANT
Filed April 29, 1952 2 Sheets-Sheet 1
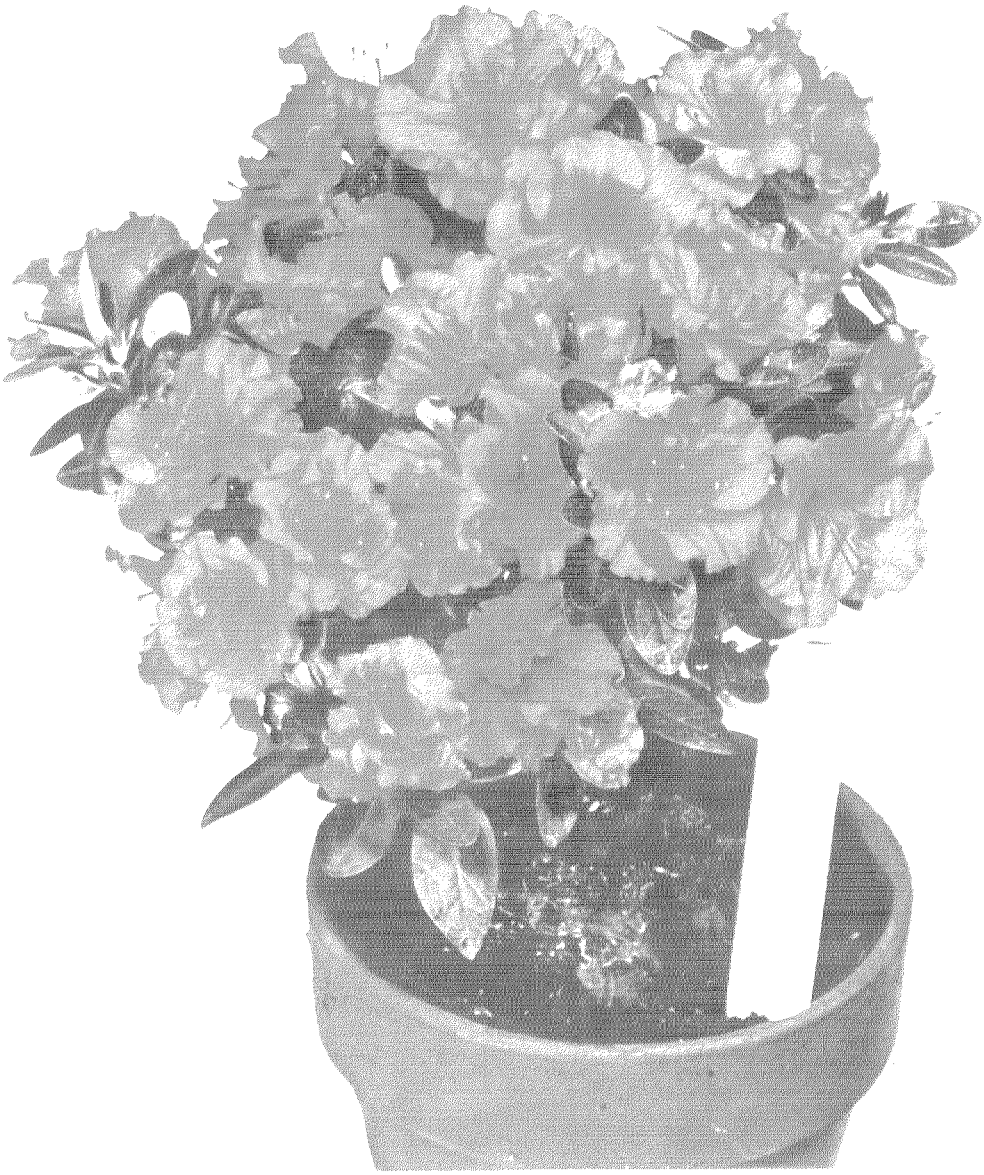
INVENTOR
MAURITS L.V. VAN ZANTEN
BY F.R. Geisler
ATTORNEY AZALEA PLANT
Filed April 29, 1952 2 Sheets-Sheet 2
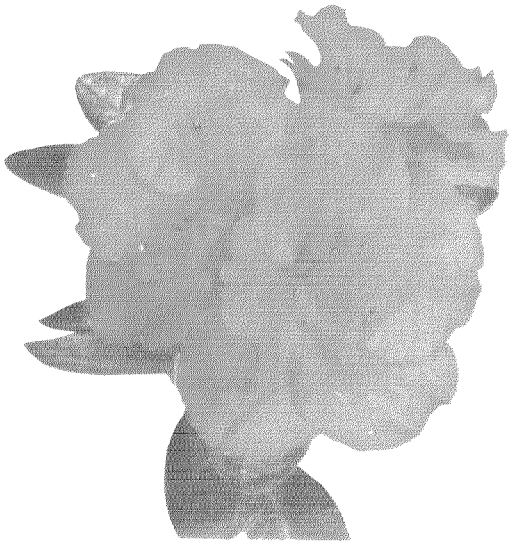
INVENTOR
MAURITS L.V. VAN ZANTEN
BY F.R. Geiler
ATTORNEY Patented Dec. 15, 1953

Plant Pat. 1,233

UNITED STATES PATENT OFFICE 1,233

AZALEA PLANT

Maurits L. V. Van Zanten, Lynden, Wash.

Application April 29, 1952, Serial No. 284,895

1 Claim. (Cl. 47—60)

This invention comprises a new and distinct variety of azalea, the result of a cross between a Sander (Hexe) variety, unpatented, and an Indica known as "Memoire de Charles Vuylsteke," unpatented, the latter being used as the female plant. The purpose of developing the new variety was to produce an earlier flowering azalea, with large flowers, which would be easy to grow and have good forcing qualities, so that it would be an attractive blooming plant for the Christmas holiday trade.

Cross pollination was performed by me on March 17, 1945, by simply removing stamens of female plant and hand-pollenizing stigma with pollen of male plant. Inspection with magnifying glass showed that pollen was properly distributed on the stamenhead without damaging this part. The fertilized plant was placed on a shelf in a warm greenhouse and properly cared for. After one week the petals of the fertilized flower wilted (indicating that fertilization had taken place) and were removed. This cross-pollenization took place in my greenhouse in Lynden, Washington. The resulting seed was collected in the fall of the same year and planted in the spring of 1946. The seedlings produced in this manner were observed for a period of two years and this particular hybrid was selected and segregated.

Cuttings were made by me from the selected seedling in Lynden, Washington, and the results for the following three successive flowering seasons were found to be always constant.

The accompanying illustrations accurately show one of these plants in bloom and a close-up view of the flowers.

The following is a detailed description of the plant and its flowers:

*Form.*—Dense, compact form, similar to the Hexe in general, but firmer wood and heavier branches.

*Foliage.*—The color of the top side of the foliage is about midway between Partially Green (00962) and Ivy Green (0001060–3), (Horticulture Chart HCC.0–21, pages 193 and 200). The underside of the leaves is a Willow Green (000862–1), (Horticulture Color Chart page 199). The points or tips of the foliage are rounded and the foliage is dense and strong in texture and keeps well under shipping conditions, thus making the plant suitable for long distance shipping. The foliage is larger than that of the Hexe.

*Flowers.*—Distinct claret-rose color (Horticulture Color Chart HCC.0–21, page 109), with a darker center. The flowers are about twice the size of those of the Hexe variety and average at least two inches across. The overall length of the petals is $1\frac{1}{2}$ inches on the average and the overall width is $1\frac{5}{16}$ inches on the average. The lower part of each petal is grown together with the lower part of the next petal. The stamens are brown red, with black heads and covered with white pollen. The stigma is dark cherry-red. The flowers are of semi-double structure, ten-petaled, with gently ruffled edges. It is a profuse bloomer. Unlike other azaleas forcing of this plant does not reduce the size of the flowers or cause the color to become less vivid.

*Characteristics of growth and blooming.*—The plant is easy to grow and grows rapidly and much faster than the Hexe. The time of flowering is from December 15, under ordinary forcing conditions, and from then on until spring. The plant is well suited for forcing and responds easily. No pre-cooling or other artificial means are required in the forcing, and not more than 60° F. greenhouse temperature at night is needed for forcing. The plant is long flowering.

Having thus disclosed my invention, I claim:

The new and distinct variety of azalea plant substantially as herein disclosed, characterized particularly by its early blooming and forcing qualities, its large size, semi-double, ten-petaled flowers of claret-rose color with darker center, and its compact growth.

MAURITS L. V. VAN ZANTEN.

No references cited.